United States Patent
Heinz et al.

(10) Patent No.: US 6,485,474 B1
(45) Date of Patent: Nov. 26, 2002

(54) CLOSURE ARRANGEMENT FOR A DISPOSABLE SYRINGE

(75) Inventors: Jochen Heinz, Vendersheim (DE); Michael Spallek, Ingelheim (DE)

(73) Assignee: Schott Glas, Mainz (DE)

( * ) Notice: Subject to any disclaimer, the term of this patent is extended or adjusted under 35 U.S.C. 154(b) by 52 days.

(21) Appl. No.: 09/715,135

(22) Filed: Nov. 20, 2000

(30) Foreign Application Priority Data

Nov. 19, 1999 (DE) .......................................... 199 55 652

(51) Int. Cl.[7] .............................................. A61M 5/00
(52) U.S. Cl. ...................... 604/263; 604/198; 604/199; 128/919
(58) Field of Search ................................. 604/192, 263, 604/198, 199; 128/917, 919

(56) References Cited

U.S. PATENT DOCUMENTS

| | | | |
|---|---|---|---|
| 4,300,678 A | * 11/1981 | Gyure et al. ............... | 206/364 |
| 4,728,321 A | * 3/1988 | Chen .......................... | 604/110 |
| 4,735,311 A | * 4/1988 | Lowe et al. ............... | 206/365 |
| 4,964,866 A | * 10/1990 | Szwarc ...................... | 604/192 |
| 4,986,818 A | * 1/1991 | Imbert et al. ............. | 604/192 |
| 5,085,647 A | * 2/1992 | Henderson et al. ....... | 604/192 |
| 5,135,514 A | 8/1992 | Kimber | |
| 5,147,328 A | 9/1992 | Dragosits et al. | |
| 5,522,812 A | 6/1996 | Talonn et al. | |
| 5,980,495 A | * 11/1999 | Heinz et al. ............... | 128/919 |

FOREIGN PATENT DOCUMENTS

| | | |
|---|---|---|
| DE | 2717830 | 3/1977 |
| DE | 8906101 | 8/1989 |
| DE | 195 37 163 | 1/1997 |
| DE | 297 08 314 | 10/1997 |
| EP | 0716860 | 6/1996 |
| EP | 0830868 | 3/1998 |
| EP | 0917882 | 5/1999 |

\* cited by examiner

*Primary Examiner*—Brian L. Casler
*Assistant Examiner*—Mark Han
(74) *Attorney, Agent, or Firm*—Walter Ottesen

(57) ABSTRACT

A cap of a closure arrangement of a prefilled disposable syringe is only removed in advance of utilizing the syringe. The disposable syringe has a syringe body (2, 3) and an injection needle (4) integrated in this body. The closure arrangement includes a stiff plastic cap (5) pushed onto the syringe head (2) and includes a lining (6) in the interior thereof which seals the needle tip. In another syringe type without integrated needle, a connecting cone of a conical connection is formed on the syringe body. The closure arrangement includes an elastomeric closure cap (tip-cap) seated on the connecting cone. The closure cap is covered by a stiff plastic cap connected to the syringe body. In both types of disposable syringes, the plastic cap is welded or cemented while forming a desired break location (7) with the syringe body (2, 3).

4 Claims, 1 Drawing Sheet

CLOSURE ARRANGEMENT FOR A DISPOSABLE SYRINGE

FIELD OF THE INVENTION

The invention relates to a closure arrangement for a prefillable disposable syringe made of plastic having an injection needle which is tightly connected in the outlet end of the syringe body. The closure arrangement includes an outer stiff plastic cap made of hard elastic material. The plastic cap can be seated on the syringe body and encloses the injection needle. In the region of at least the needle tip, the plastic cap is provided in its interior with a sealing lining made of a soft elastic material.

The invention also relates to a closure arrangement for a prefillable disposable syringe made of plastic wherein the closure arrangement includes a connecting cone of a conical connection with the connecting cone being formed on the outlet end of the syringe body. The closure arrangement includes an elastomeric closure cap seated on the connecting cone and the closure cap is covered by an outer stiff plastic cap connected to the injection body.

BACKGROUND OF THE INVENTION

Prefilled disposable syringes having an integrated injection needle must be provided with a needle cap during storage to protect the injection needle and the syringe content irrespective of whether the syringe is made of glass or of plastic. The needle cap is only removed directly in advance of the application. These disposable syringes are, inter alia, described in well known standards wherein the injection needle is called an injection cannula and the needle cap is characterized as a protective cap. These syringes are typically manufactured for medical purposes (pharmaceutical and diagnostic) but also are made for cosmetic purposes.

Needle caps for the above-mentioned disposable syringes are known in many embodiments. The so-called classical embodiments, which are the widest known, are needle caps which are made of an elastomer, preferably rubber or natural rubber. The length is selected so that the tip of the injection needle sticks into the cap tip when the cap is seated and remains tightly closed by the material of the cap. Such a needle cap is disclosed in combination with an injection needle integrated into the injection head, for example, as shown in German patent publication 2,717,830 (FIG. 6). This needle cap has, on the one hand, the advantageous characteristic that it can be simply pushed onto the syringe head and can be completely pulled off without preparatory steps because the elastic cap skirt fits snugly and sealingly against the syringe head and thereby provides a reliable microbiological seal. The cap however has, on the other hand, several disadvantageous characteristics:

(a) The needle cap can only counter mechanical effects to a limited extent because of the softness of the material. The needle cap can also be penetrated with the handling by the user which can constitute a considerable danger of injury for the user.

(b) The needle cap is pressed together when being pulled off and comes to lie tightly against the cannula surface. This leads to at least partially stripping off the silicone applied to the needle. This silicone is intended as a sliding means during the injection operation. If this slide means is not there, the injection is painful for the patient during the injection process. Furthermore, silicone particles or droplets can form which can get into the body.

(c) The automated assembly of the needle cap is difficult because a reliably controllable path limit for the push-on operation is not present so that it can easily happen that the needle is pushed on too far or not far enough onto the syringe head. Both cases are most disadvantageous because, in the first case, the needle can penetrate through the needle cap and, in the second case, a microbiological reliable seal is no longer ensured.

(d) In the seated condition, the injection needle cannot be controlled by the user or judged, for example, whether the needle is the one suitable for the intended purpose or whether the needle is bent or damaged or contaminated. For this purpose, the needle cap must be pulled off and, if required, must be pushed on again with the very substantial danger of microbiological contamination of the needle or even of the syringe content, penetrating the needle cap and/or a bending of the needle.

(e) After pulling off the needle cap, it can be simply reseated, that is, no original sealing is guaranteed.

(f) By pulling off the needle cap, an underpressure is generated at the needle tip so that the liquid filled in the syringe can easily discharge. For the user, it is necessary to remove this liquid drop which would reduce the actual applied dose and, on the other hand, the external needle surface becomes wetted with the medicine. In this way, and during injection, medicine enters the insert channel undefined and this is generally unwanted and, for some medicines, can lead to hematomas at the injection location. Such medicines are, for example, anti-coagulants (heparin, et cetera).

To counter the above disadvantages (a) to (f), German patent publication 8,906,101 discloses a needle cap consisting of a plastic cap of a relatively hard elastic material which, on the inside, is lined with a soft elastic sealing material at least in the region of the cannula tip. In this way, this soft elastic material can be selected for optimal sealing characteristics (sealing function); whereas, the hard elastic material is more suitable to counter mechanical effects (protective function).

The invention proceeds from a needle cap of this type insofar as it relates to a prefillable disposable syringe having an integrated injection needle.

In addition to plastic disposable syringes having an integrated injection needle, also such disposable syringes are known which have a connecting cone of a cone connection, a so-called Luer lock cone connection in accordance with DIN ISO 594. The connecting cone is formed on the outlet end of the syringe body. In the case of an application, a separate needle holder can be seated on this connecting cone.

The closure arrangement for this syringe type typically comprises an elastomeric closure cap which is covered by an external stiff plastic cap made of hard elastic material. The closure cap, a so-called tip cap, is seated on the connecting cone.

It is from this kind of cap that the invention proceeds insofar as it relates to an injection body without a needle. This kind of closure arrangement is disclosed, for example, in European patent publication 0,716,860 or in German patent publication 195 37 163.

In both syringe types, the closure system is typically releasably attached via backcuts or projections on the syringe body.

This type of attachment is very complex during manufacture. The type of attachment makes it necessary to operate with high precision with respect to the syringe body as well as the closure arrangement in order to ensure that, for example, the closure arrangement does not drop off or loosen because of the thermal expansion of the entire system, for example, because of a sterilization of the filled and closed syringe such as in an autoclave at 121° C./20 minutes in accordance with the requirements of medical standards or that this leads to a closure arrangement which is microbiologically untight.

The following is also considered. Often, the requirement is present that it must be ensured that the disposable syringe cannot be used again. This leads to the necessity of ensuring that a closure system, once opened, cannot be returned to its original state.

Such "original closures" (manufacturer's seal) are, for example, known for the syringe type having an integrated needle from German patent publication 297 08 314 and for the syringe type having a connecting cone from European patent publications 0,917,882 and 0,830,868 (in addition to the already mentioned publications, German patent publication 195 37 163 and European patent publication 0,716, 860).

In all these known cases, as with the closure arrangements without an original seal, the external stiff plastic cap is mechanically fixed on the syringe body by backcuts and/or projections and has the disadvantageous consequences already mentioned initially herein.

SUMMARY OF THE INVENTION

It is an object of the invention to provide a simple and reliable closure arrangement for a prefillable disposable syringe made of plastic with and without an integrated needle which requires no back cuts or projections for mechanically fixing the closure arrangement on the syringe body and which is configured as an original closure.

The closure arrangement of the invention is for a prefillable disposable syringe made of plastic. The disposable syringe includes a syringe body having a discharge end and an injection needle having a needle tip and the injection needle is fixedly connected to the discharge end. The closure arrangement includes: an outer stiff plastic cap made of hard elastic material; the plastic cap defining an interior and being seated on the syringe body so as to encase the injection needle; a sealing lining disposed in the interior at least in the region of the needle tip and the sealing lining being made of a soft elastic material; the plastic cap and the syringe body conjointly defining a joining interface; and, separable joining means formed at the joining interface to connect the plastic cap to the syringe body so as to permit a user to separate the plastic cap from the syringe body.

In another embodiment, the closure arrangement includes: a connecting cone being formed on the discharge end; an elastomeric closure cap seated on the connecting cone; a stiff plastic cap covering the closure cap and the plastic cap and the syringe body conjointly defining a joining interface; and, separable joining means formed at the joining interface to connect the plastic cap to the syringe body so as to permit a user to separate the plastic cap from the syringe body.

The measures in accordance with the invention provide a simple but reliable connection via the welding or gluing operations, which are relatively simple to carry out in a manufacturing context. This reliable connection fixes the closure arrangement even when there is increased internal pressure in the vessel which occurs during autoclaving and thereby guarantees the seal tightness and especially the microbiological seal tightness and requires no backcuts and/or projections because of the fixing of planar surfaces.

Once the closure arrangement is opened by breaking though the separation location, the closure arrangement cannot again be returned to its original condition at least not with the means available to a user. Desired separation locations in the context of original seals are known from the publications cited initially herein.

BRIEF DESCRIPTION OF THE DRAWING

The invention will now be described with reference to the drawings wherein.

DESCRIPTION OF THE PREFERRED EMBODIMENTS OF THE INVENTION

Figure 1:
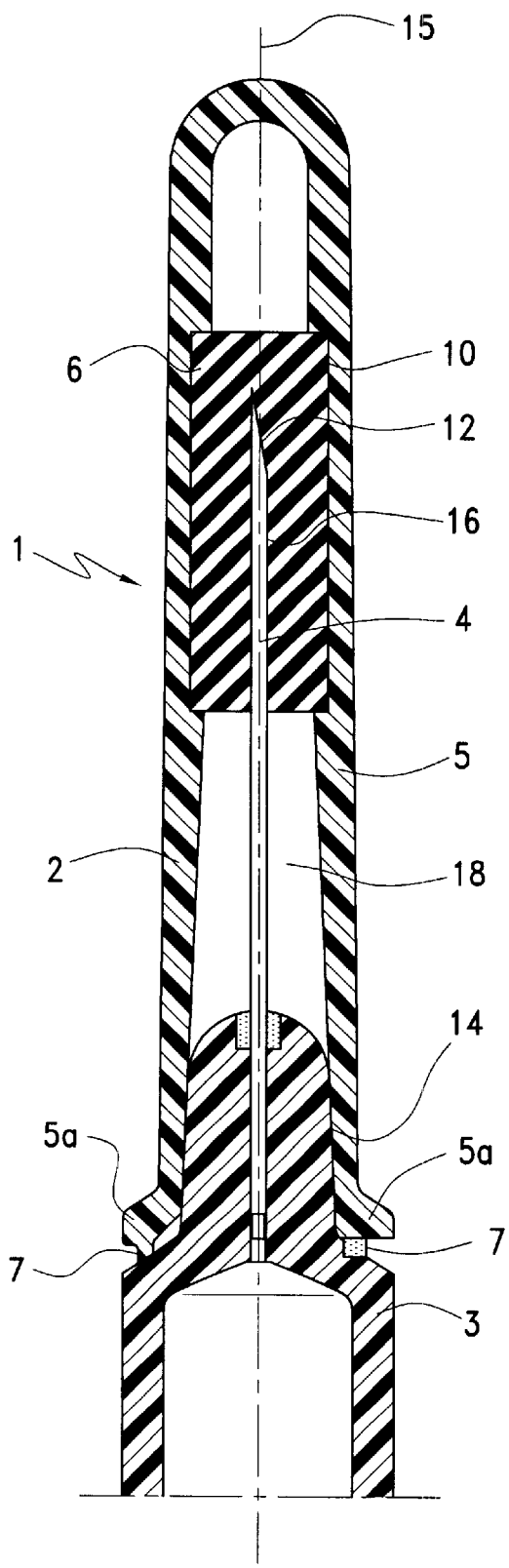
FIG. 1 shows a closure arrangement according to the invention applied to a prefillable disposable syringe having an injection needle tightly connected into the syringe head; and, FIG. 2 shows the closure arrangement according to the invention applied to a disposable syringe without an integrated injection needle.

The closure arrangement is identified by reference numeral 1 in FIG. 1 and is configured as a needle cap. The closure arrangement is for a prefillable disposable syringe having an injection needle 4 tightly connected in the syringe head 2 of a plastic syringe body 3 of the disposable syringe. The needle cap comprises two parts, namely, an outer plastic cap 5 and a sealing lining 6 in the inside of the cap in the region of the needle tip. The plastic cap 5 can be made, for example, of transparent polymers such a cycloalkene copolymer (COC), polystyrene, polyethylene terephthalate (PET), polyethylene naphthylate (PEN), polymethyl pentene (TP), acryl butadiene styrol (ABS), polycarbonate (PC) or semitransparent polymers such as polyethylene or polypropylene. The sealing lining 6 is made of a soft elastic material such as natural rubber, halogen butyl elastomer, preferably, a translucent rubber-like elastomer, for example, silicone rubber, thermoplastic elastomers, COC elastomers. The lining is accommodated form-tight in a corresponding recess 10 of the plastic cap 5.

In another embodiment, it is possible, with a two-component injection-molding method to produce, in one method step, the external jacket from one of the above-mentioned plastics and the lining with a soft elastic thermoplastic elastomer (TP) or silicone rubber.

The needle tip 12 is sealed by the lining 6 in that the needle is stuck into this part when pushing the needle cap 5 onto the syringe head 2.

The plastic cap 5 has a peripheral collar 5a. This collar and the syringe body 3 conjointly define a separable connecting or joining interface at 7. The collar 5a is securely mechanically connected over its entire periphery to the syringe body 3 while forming a peripherally extending desired separation location 7. The mechanical connection also ensures the necessary microbiological seal.

The connection can be provided in that the plastic cap 5 is welded directly to the plastic syringe body 3, for example, with ultrasonic welding or laser welding or induction welding depending upon the plastic material or manufacturing possibilities.

The direct connection can be provided also by cementing, for example, with an adhesive, especially epoxy resin, which can be cured with the aid of electromagnetic radiation.

The above-mentioned type of joining requires no back cuts or projections as in the known closure arrangements. This joining ensures a simple but yet reliable closure for disposable syringes without the disadvantages described initially herein.

The joining ensures, in addition, an original closure, that is, it provides a closure system which, after it is once opened, cannot again be returned to its original state.

In FIG. 1, a plastic disposable syringe is shown with an integrated injection needle 4. The invention can, however, also be applied to plastic disposable syringes which have no integrated injection needle but have a connecting cone, a so-called Luer or Luer lock cone connection in accordance with standard ISO 594 for a separate needle attachment.

In such a case, an elastomeric closure cap, a so-called "tip cap" is seated on the connecting cone in the usual manner. The closure cap is, in turn, covered with a hard plastic cap corresponding to cap 5 in FIG. 1. This hard plastic cap is then, as described above, welded or cemented to the syringe body while forming a desired break or separation location.

The needle cap 5 in FIG. 1 preferably comprises a transparent plastic material whereby a visual inspection of the injection needle with the seated needle cap can be made.

The syringe head 2 and the needle cap 1 are configured so as to be matched to each other in an advantageous manner so that, when pulling off the plastic cap 5 with the inner lining 6, the opening in the needle tip 12 is only then cleared of the soft elastic inner lining 6 of the plastic cap 5 when the cap interior is opened to provide a pressure compensation, that is, the pressure in the interior cap corresponds to the external air pressure.

In this way, a drop-free removal of the needle cap 1 is possible because no underpressure can develop at the opening of the needle tip 12 which is a very substantial advantage.

Constructively, the drop-free removal is ensured in that seal distance for the needle tip in the lining 6 is greater than the seal distance of the needle cap 1 on the syringe head 2.

The plastic cap 5 and the syringe body or syringe head 2 conjointly define a first sealing interface 14 extending in the direction of the longitudinal axis 15. The sealing lining 6 and the needle tip 12 conjointly define a second sealing interface 16 with the sealing lining 6 extending in the direction of the longitudinal axis 15. The sealing lining continues to seal off the opening in needle tip 12 as the cap 5 is pulled off the syringe head 2. The first sealing interface 14 has an axially extending sealing length relative to the second sealing interface 16 to ensure that the interior 18 of the plastic cap 5 becomes pressure compensated as the plastic cap is pulled off the syringe body 2 before the sealing lining 6 clears the needle tip 12. That is, the sealing interface 16 is longer than the sealing interface 14.

In the embodiment of FIG. 1, the external plastic cap 5 is closed on all sides. The introduction of the inner soft elastic lining 6 is therefore only possible at the syringe head end via the corresponding opening in the outer plastic cap 5.

Embodiments are also conceivable wherein the outer plastic cap 5 has a cutout at the tip which can be tightly closed by the inner soft elastic lining 6.

The lining can close off flush with the cap 5 or can project somewhat therefrom.

In this way, the assembly of the needle cap from its two components is facilitated, for example, in that the inner lining can be reliably held at its exposed end.

This embodiment makes possible an assembly of the inner lining 6 from the cap tip which, under some circumstances, can be more advantageous than the type of assembly of FIG. 1.

Figure 2:
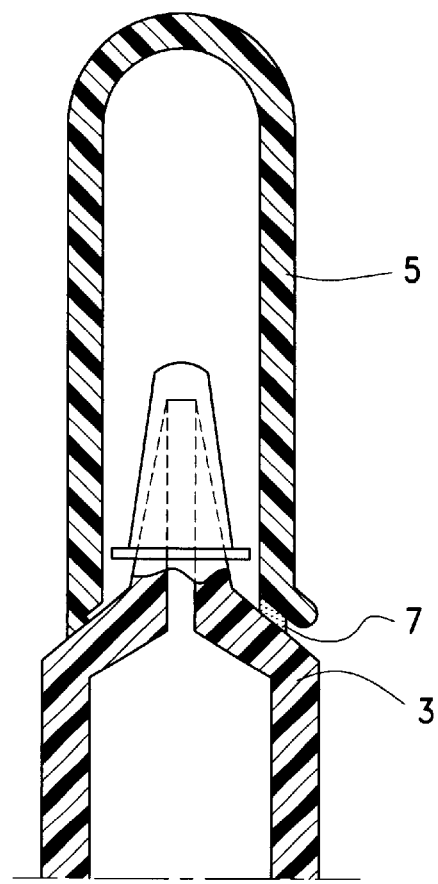

FIG. 2 is a schematic showing another syringe type without an integrated needle. Here too, the stiff plastic cap 5 and the syringe body conjointly define a joining interface whereat a peripherally extending weld or adhesive seal is formed at the joining interface 7 to connect the stiff plastic cap 5 to the syringe body 3 while at the same time defining a predetermined break zone so as to permit a user to manually break the seal to separate the stiff plastic cap 10 from the syringe body 3.

It is understood that the foregoing description is that of the preferred embodiments of the invention and that various changes and modifications may be made thereto without departing from the spirit and scope of the invention as defined in the appended claims.

What is claimed is:

1. A closure arrangement for a prefillable disposable syringe made of plastic, the disposable syringe including a syringe body having a discharge end and an injection needle having a needle tip and said injection needle being fixedly connected to said discharge end, the closure arrangement comprising:

an outer stiff plastic needle-protective cap made of hard elastic material;

said plastic needle-protective cap defining an interior and being seated on said syringe body so as to encase said injection needle;

a sealing lining disposed in said interior at least in the region of said needle tip and said sealing lining being made of a soft elastic material;

said plastic needle-protective cap and said syringe body conjointly defining a joining interface; and, a peripherally extending weld or adhesive seam formed at said joining interface to connect said plastic needle-protective cap to said syringe body and to define a predetermined break zone so as to permit a user to manually break said seam to separate said plastic needle-protective cap from said syringe body.

2. The closure arrangement of claim 1, said plastic cap defining a longitudinal axis; said plastic cap and said syringe body conjointly defining a first sealing interface extending in the direction of said longitudinal axis; said sealing lining and said needle tip conjointly defining a second sealing interface with said sealing lining extending in the direction of said longitudinal axis for a pregiven length; said first sealing interface having an axially extending sealing length relative to the pregiven length of said second sealing interface to ensure that said interior of said plastic cap becomes pressure compensated as said plastic cap is pulled off said syringe body before said sealing lining clears said needle tip.

3. The closure arrangement of claim 1, wherein said plastic cap is closed on all sides thereof.

4. A closure arrangement for a prefillable disposable syringe made of plastic, the disposable syringe including a syringe body having a discharge end, the closure arrangement comprising:

a connecting cone formed on said discharge end;

an elastomeric closure cap seated on said connecting cone;

a stiff plastic cap covering said elastomeric closure cap and said stiff plastic cap and said syringe body conjointly defining a joining interface; and, a peripherally extending weld or adhesive seam formed at said joining interface to connect said stiff plastic cap to said syringe body and to define a predetermined break zone so as to permit a user to manually break said seam to separate said stiff plastic cap from said syringe body.

* * * * *